United States Patent
Bolleter et al.

(10) Patent No.: US 10,390,909 B2
(45) Date of Patent: Aug. 27, 2019

(54) PROSTHESIS SYSTEM

(71) Applicant: DENTALPOINT AG, Zürich (CH)

(72) Inventors: Philip Bolleter, Zürich (CH); Pascal Wettstein, Villmergen (CH)

(73) Assignee: DENTALPOINT AG, Zurich (CH)

( * ) Notice: Subject to any disclaimer, the term of this patent is extended or adjusted under 35 U.S.C. 154(b) by 0 days.

(21) Appl. No.: 15/575,287

(22) PCT Filed: Jun. 7, 2016

(86) PCT No.: PCT/EP2016/062873
§ 371 (c)(1),
(2) Date: Nov. 17, 2017

(87) PCT Pub. No.: WO2016/198385
PCT Pub. Date: Dec. 15, 2016

(65) Prior Publication Data
US 2018/0147030 A1 May 31, 2018

(30) Foreign Application Priority Data

Jun. 8, 2015 (CH) .......................................... 817/15

(51) Int. Cl.
*A61C 8/00* (2006.01)
(52) U.S. Cl.
CPC ............ *A61C 8/0068* (2013.01); *A61C 8/005* (2013.01); *A61C 8/0057* (2013.01); *A61C 8/0074* (2013.01)

(58) Field of Classification Search
CPC ..... A61C 8/0068; A61C 8/0057; A61C 8/005; A61C 8/0074; A61C 8/0086; A61C 8/0012; A61C 8/0066; A61C 8/006
See application file for complete search history.

(56) References Cited

U.S. PATENT DOCUMENTS 6,464,500 B1 * 10/2002 Popovic ............... A61C 8/0022
433/173
7,942,670 B2 * 5/2011 Marley ................. A61C 8/0068
411/910

(Continued)

FOREIGN PATENT DOCUMENTS

DE 299 21 193 U1 4/2001
EP 0 535 190 A1 4/1993
(Continued)

*Primary Examiner* — Wade Miles
*Assistant Examiner* — Shannel N Wright
(74) *Attorney, Agent, or Firm* — Pauley Erickson & Kottis (57) ABSTRACT

The invention relates to a dental prosthesis system that includes a ceramic implant for osseointegration in a jaw bone with a receiving opening for a connection screw and an abutment, preferably made of a ceramic, wherein the abutment can be secured in the receiving opening of the implant by the connection screw made of fiber-reinforced thermoplastic. A screw lock includes first interlocking elements and second interlocking elements, wherein the first interlocking elements are arranged on the connection screw and the second interlocking elements are arranged in the receiving opening of the implant and/or on the abutment. When tightening or releasing the connection screw in the implant, the first interlocking elements are elastically deformed in conjunction with the second interlocking elements.

14 Claims, 9 Drawing Sheets

Section A-A (56) References Cited

U.S. PATENT DOCUMENTS

| | | | | |
|---|---|---|---|---|
| 2003/0224330 A1* | 12/2003 | Aravena | ............... | A61C 8/005 433/173 |
| 2003/0224331 A1* | 12/2003 | Kumar | .................. | A61C 8/005 433/173 |
| 2006/0216672 A1 | 9/2006 | Dinkelacker | | |
| 2008/0286721 A1* | 11/2008 | Walther | ............... | A61C 8/0012 433/174 |
| 2009/0111072 A1 | 4/2009 | Lombardo et al. | | |
| 2009/0123888 A1* | 5/2009 | Rosenberg | ........... | A61C 8/0048 433/173 |
| 2012/0219928 A1* | 8/2012 | Abboud | ................ | A61C 8/005 433/174 |
| 2012/0288825 A1* | 11/2012 | Nordin | ................... | A61C 8/005 433/173 |
| 2013/0309630 A1* | 11/2013 | Bolleter | ................ | A61C 8/005 433/173 |
| 2015/0132717 A1 | 5/2015 | Seo et al. | | |
| 2015/0147721 A1* | 5/2015 | Costa Codina | ........ | A61C 8/005 433/174 |
| 2015/0147724 A1 | 5/2015 | Staudenmann et al. | | |

FOREIGN PATENT DOCUMENTS

| | | | |
|---|---|---|---|
| EP | 2 522 300 A1 | 11/2012 | |
| WO | WO 92/18780 A1 | 10/1992 | |
| WO | WO 2004/032786 A1 | 4/2004 | |
| WO | WO 2014/091346 A2 | 6/2014 | |
| WO | WO 2016006730 A1 * | 1/2016 | ............... A61C 8/00 |

* cited by examiner

FIG. 1A

Section A-A

FIG. 1B

Section B-B

Section A-A
FIG. 5B

PROSTHESIS SYSTEM

BACKGROUND OF THE INVENTION

Field of the Invention

The invention relates to a dental prosthesis system, in particular a dental prosthesis system with a screw lock.

Discussion of Related Art

In the field of dental implantology, systems made of titanium are still used predominantly. These systems usually consist of an implant, abutment and connection screw. Following osseointegration of the implant, the abutment is connected to the implant in the axial direction by means of a connection screw and tightened with a torque of approximately 20 to 35 Ncm. The implant and abutment generally have what are known as positioning faces, which establish a rotationally fixed connection and are used to secure the abutment with respect to torsional forces that occur during chewing. In the case of known titanium implants, a loss of pre-tension force at the connection screw and consequently a loosening of the abutment or the secondary part are caused by high mechanical loads that occur during chewing and by the resultant bending moments. Since the access to the head of the connection screw is usually concealed by a cemented crown, this crown must be destroyed in order to re-tighten a loosened screw. Furthermore, a slow and steady loosening of the connection screw can lead to continuous damage of the abutment and of the implant. In order to prevent a loosening of the connection screw in systems made of titanium, a screw is used in accordance with the prior art, which screw has a flat-conical screw head. If the abutment is fixed in the implant, the flat-conical screw head acts as a self-locking screw connection in conjunction with a through-bore in the abutment, which bore is likewise flat-conical. Loosening is in this way counteracted.

The high-performance ceramic zirconium dioxide has become established in dental implantology as a relatively young material compared to the known systems formed of titanium. The screw lock known from the prior art for titanium with flat-conical screw locking is not suitable for ceramic due to the outwardly directed forces that occur with this locking. In addition, compared to systems made of titanium, dental prosthesis systems made of ceramic cannot be exposed to tensile loads. Solutions that are intended to prevent a loosening of connection screws that are used in ceramic dental prosthesis systems are known from the prior art.

Document WO2014091346 A2 discloses a screw for fixing an abutment to an implant. The implant has an internal bore with a thread. The screw is formed incongruently relative to this thread, in particular if the screw is made of plastic. The incongruence means that, besides the screw body being cut into (the implant body and thread thereof are harder), there is also a cold welding between the screw and implant body, and therefore a secure fit of the screw is ensured. The connection described in WO2014091346 A2 has the disadvantage that, in order to release this connection, the screw must be drilled out, since a reversible disconnection is not possible on account of the deformation of the screw body.

EP2522300A describes an abutment for receiving a dental prosthesis, wherein the abutment is made of a glass-fibre-reinforced resin. The abutment has a connection element, which in a preferred embodiment is screwed into the implant. The implant can be made here optionally of titanium, stainless steel, ceramic or another material for osseointegration in a jaw bone. Chewing forces should be absorbed to be best possible extent by means of the material used for the abutment, and the risk of breakage thus minimized. In order to increase the stability of the dental prosthesis system, the use of a plastic cement is proposed. There is no mention of the problem that, due to the different materials used for abutment and implant, there is an increased likelihood that the connection screw can loosen over the period for which the dental prosthesis system is worn.

SUMMARY OF THE INVENTION

One object of the present invention is to provide a dental prosthesis system which does not have the disadvantages of the prior art. A further object of the dental prosthesis system according to the invention is to prevent a loosening of the abutment in the ceramic implant over the period for which the dental prosthesis system is worn.

These objects are achieved by the features of claim 1 and the dependent claims.

Where reference is made hereinafter to a screw which is used to fix the abutment in the implant, this means a screw which remains permanently in the patient's mouth and which is exposed to prolonged stress by chewing forces.

In order to solve the stated objects, a dental prosthesis system is proposed in accordance with the invention which has a ceramic implant for osseointegration in a jaw bone with a receiving opening for a connection screw made of fibre-reinforced thermoplastic for securing the abutment. The dental prosthesis system according to the invention comprises a screw lock, wherein the screw lock has a first interlocking means and a second interlocking means, wherein the first interlocking means is arranged on the connection screw and the second interlocking means is arranged in the receiving opening of the implant and/or on the abutment. When tightening or releasing the connection screw, the first interlocking means is elastically deformed in contact with the second interlocking means.

Due to the elastic deformability of the first interlocking means and due to the fact that said means is manufactured in an oversized manner, the first interlocking means compresses and relaxes in conjunction with the second interlocking means when tightening or releasing the connection screw. With the elastic deformability, any effective torsional forces are negligibly small.

During the tightening or releasing of the connection screw, it is necessary to overcome compression forces. It has been found that the torque required to initially release the connection screw is greater than the maximum tightening moment which must be applied in order to tighten the screw. With the dental prosthesis system according to the invention, a loss of pre-tension force at the connection screw can be counteracted.

A preferred end position of the connection screw or the first interlocking means is to be understood to mean the position in which the first interlocking means fully engages in the second interlocking means. Immediately before the end position is reached, the connection screw is acted on by the desired maximum tightening moment. Immediately before this maximum tightening moment is reached, the first interlocking means engages in the second interlocking means and the tightening moment decreases.

A further end position, which is different from the preferred end position, is understood to be that in which the desired maximum tightening moment acts directly on the connection screw and the first interlocking means are compressed in conjunction with the second interlocking means.

In one embodiment the first interlocking means is rotatable relative to the second interlocking means. When a first rotary position is reached, the first interlocking means is compressed in conjunction with the second interlocking means, and relaxes when a second rotary position is reached. In an end position the first interlocking means engages fully in the second interlocking means.

In a preferred embodiment the first interlocking means is formed as a multi-edged outer profile on the connection screw and the second interlocking means is formed as a multi-edged inner profile, preferably a triangular profile, formed in the receiving opening of the implant. When a tightening moment is applied to the connection screw, the edge regions of the multi-edged outer profile which are in contact with the side faces of the multi-edged inner profile are elastically deformed. If the edge region of the multi-edged outer profile contacts the side face of the multi-edged inner profile as the tightening moment of the connection screw is applied, the multi-edged outer profile is compressed. If the application of the tightening torque continues, the multi-edged outer profile rotates in the multi-edged inner profile into a position in which the side faces of the multi-edged outer profile contact the side faces of the multi-edged inner profile. The edge regions of the multi-edged outer profile relax. A relaxation of this kind occurs for example in the end position when the multi-edged outer profile fully engages in the multi-edged inner profile. Just before the engagement, the desired maximum tightening moment is reached, which decreases accordingly in the engaged state.

The multi-edged outer profile, preferably a polygon, is preferably manufactured in an oversized manner in relation to the multi-edged inner profile, preferably a triangular profile. In particular, the edge regions of the multi-edged outer profile are compressed and relaxed again as the torque is applied. The multi-edged outer profile therefore may not exceed a certain size in relation to the multi-edged inner profile, since this could lead otherwise to damage to the fibre-reinforced thermoplastic material.

In a preferred embodiment the multi-edged inner profile in the implant is a triangular profile. In the example below, an inner circle radius of the triangular inner profile of $$r_{ID} = 0.85 \text{ mm}$$

is assumed.

For the formulas below, with which the outer circle radius and the inner circle radius of a multi-edged outer profile can be calculated, at which the fibre-reinforced thermoplastic is compressed to the maximum, but does not break, the following assumptions are made:

1. The connection screw does not expand in the axial direction on account of the fibre reinforcement
2. The material is merely compressed; shear and torsional forces are ignored
3. The fibres have no influence on the elastic, radial compression behaviour of the matrix
4. The material behaves radially identically under tension and pressure The following mathematical relationships therefore exist for the outer and inner circle radius:

$$r_{ak} = \varepsilon_{Max} \times r_{ID} + r_{ID} = r_{Impl}(\varepsilon_{Max} + 1) = r_{ID}\left(\left|\frac{\sigma_C}{E}\right| + 1\right)$$

$$r_{ik} = \cos(\alpha) \times r_{ak} = \cos\left(\frac{360°}{2n}\right) \times r_{ID}\left(\left|\frac{\sigma_C}{E}\right| + 1\right)$$

$r_{ak}$=outer circle radius of the multi-edged outer profile on the connection screw
$r_{ID}$=inner radius of the triangular inner profile in the implant $$\varepsilon_{Max} = \left|\frac{\sigma_C}{E}\right| = \text{Maximum compression according to Hooke's law}$$

$\sigma_c$=shear stress
E=E=modulus
n=number of edges of the multi-edged outer profile
$r_{ik}$=inner circle radius For the calculation example below, a fibre-reinforced thermoplastic with a PEEK matrix with a compressive strength of 118 MPa and an E-modulus of 4 GPa is assumed. According to Hooke's law and the above-cited formula, the following value is given for the outer circle radius:

$$r_{ak} = 0.875 \text{ mm}$$

The inner circle radius and the diameter of the multi-edged outer profile are dependent on the number of edges of the multi-edged outer profile (n). For a multi-edged outer profile with n=3 to n=12, the following values are given for the inner circle radius and diameter:

| n | 3 | 4 | 5 | 6 | 7 | 8 | 9 | 10 | 11 | 12 |
|---|---|---|---|---|---|---|---|----|----|----|
| angle α | 60 | 45 | 36 | 30 | 25.7 | 22.5 | 20 | 18 | 16.4 | 15 |
| r_ik | 0.44 | 0.62 | 0.71 | 0.76 | 0.79 | 0.81 | 0.82 | 0.83 | 0.84 | 0.85 |
| d_ik | 0.88 | 1.24 | 1.42 | 1.52 | 1.58 | 1.62 | 1.64 | 1.66 | 1.68 | 1.7 |

In a preferred embodiment the multi-edged outer profile on the connection screw is arranged at a screw end opposite the screw head. For example, it is also possible to position the multi-edged outer profile directly adjacently to the screw head, which is to say between the screw head and thread.

In a further preferred embodiment of the invention the connection screw and the abutment are made in one piece from fibre-reinforced thermoplastic. The connection screw and abutment form a part. The interlocking means are arranged on the connection screw in this embodiment. The abutment does not have a through-bore.

In a further preferred embodiment of the dental prosthesis system according to the invention the first interlocking means is arranged on the head of the connection screw and the second interlocking means is arranged in a through-bore of the abutment. In an arrangement of this kind the first interlocking means for example comprises at least one rib, and the second interlocking means comprises at least one groove. The at least one rib runs on an outer peripheral surface of the head of the connection screw, and the at least one groove runs on an inner peripheral surface of the through-bore. If the at least one rib contacts the at least one groove as the tightening moment is applied, the rib relaxes and engages into the groove. In those regions of the through-bore in which there is no groove arranged, the rib is compressed as the screw is turned.

In a preferred embodiment the at least one rib is arranged on an outer peripheral surface of the head of the connection screw, and the at least one groove is arranged on an inner peripheral surface of the through-bore. The ribs and the grooves preferably run helically. In a further embodiment the at least one rib runs in the axial direction based on a vertical axis of the connection screw, and the at least one groove runs in the axial direction based on a vertical axis of the abutment.

In a further preferred embodiment the outer peripheral surface of the screw has grooves, in which ribs of the inner peripheral surface of the receiving opening engage in an interlocked manner.

In a further preferred embodiment the second interlocking means is a structure which is arranged on an inner peripheral surface of the through-bore of the abutment. This structure has protrusions, preferably teeth. The corresponding first interlocking means are preferably disposed on the head of the connection screw.

In preferred embodiments the dental prosthesis system according to the invention, in particular the receiving opening of the ceramic implant, has a portion formed as a cylindrical precision bore. The cylindrical precision bore is overlapped in the axial direction based on its rotation axis by an internal thread. The connection screw has a precision-fit cylinder corresponding to the cylindrical precision bore and an external thread corresponding to the internal thread, so that a perfect fit and/or a threaded connection are/is formed between connection screw and receiving opening.

In a preferred embodiment the cylindrical precision bore has a cylindrical proportion of from 20% to 50%, measured at the cylindrical lateral surface of the cylindrical precision bore.

In all embodiments the connection screw is manufactured from a fibre-reinforced thermoplastic. The reinforcement fibres are, for example, the following fibres: carbon fibres, aramid fibres, glass fibres, carbon nanotubes, or combinations thereof.

In a particularly preferred embodiment the fibre-reinforced thermoplastic is made of unidirectional carbon fibres in a PEEK matrix.

In those embodiments in which the second interlocking means is arranged in the through-bore of the abutment and the first interlocking means is arranged on the connection screw, an anti-twist mechanism is provided on a contact face between the abutment and a distal end of the implant, which mechanism ensures a rotationally stable positioning of the abutment.

In those embodiments in which the second interlocking means is arranged in the receiving opening of the implant and the first interlocking means is arranged on the connection screw, an anti-twist mechanism is provided on a contact face between the abutment and a distal end of the implant, which mechanism ensures a rotationally stable positioning of the abutment.

BRIEF DESCRIPTION OF SEVERAL VIEWS OF THE DRAWINGS

The invention will be explained in greater detail hereinafter on the basis of exemplary embodiments in conjunction with the drawing, in which.

DETAILED DESCRIPTION OF THE INVENTION

Figure 1A:
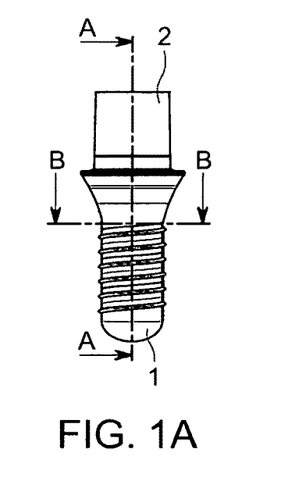
FIG. 1A shows a side view of the dental prosthesis system with implant and an abutment (connection screw and screw lock not visible)

FIG. 1A shows a side view of a first embodiment of the dental prosthesis system comprising an implant 1 and an abutment 2, which has a through-bore 10 for receiving a connection screw 7. The connection screw and the through-bore are not visible in FIG. 1A. The implant 1 and the abutment 2 are manufactured from a ceramic material, preferably zirconium oxide.

Figure 1B:
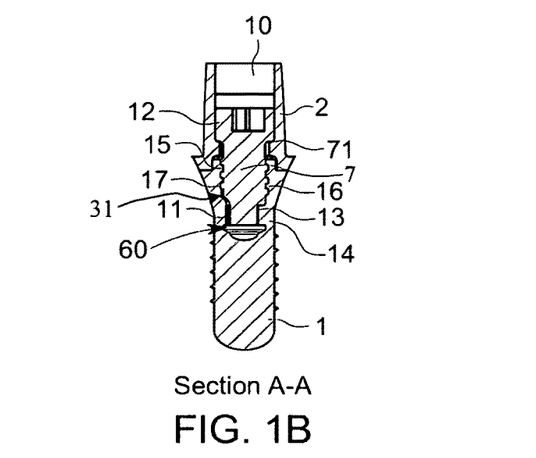
FIG. 1B shows a longitudinal section along the vertical axis A-A through an embodiment of the dental prosthesis system according to the invention with screw lock.

FIG. 1B shows a sectional illustration along the axis A-A of the embodiment from FIG. 1A. What are shown are the abutment 2 with the through-bore 10, the implant 1 and a preferred embodiment of the connection screw 7. The connection screw 7 is manufactured from a thermoplastic fibre-reinforced material. In the illustrated preferred embodiment the multi-edged outer profile 11 is disposed at the proximal end of the connection screw 7. The multi-edged outer profile 11 is manufactured in an oversized manner compared to a multi-edged inner profile 13, which is arranged in a receiving opening 14 of the implant 1. For example, the inner circle diameter of the multi-edged inner profile 13 has a value of 1.7 mm. The outer circle diameter of the multi-edged outer profile 11 is tailored thereto, measuring 1.8 to 1.9 mm.

In the illustrated embodiment the multi-edged inner profile 13 is embodied as a triangular inner profile and is arranged in the proximal region of the receiving opening 14 of the implant 1. The screw lock 60 is formed by the conjunction of the multi-edged outer profile 11 on the connection screw 7 and of the multi-edged inner profile 13. Due to the fact that the connection screw 7 is manufactured in an oversized manner, a press fit is produced. As the multi-edged outer profile 11 is screwed into the multi-edged inner profile 13 or released therefrom, there is an elastic deformation of the thermoplastic fibre-reinforced material of the multi-edged outer profile 11. As the desired torque is applied to the connection screw 7, the edge regions of the multi-edged outer profile 11 are elastically deformed and engage fully in a desired end position in the multi-edged inner profile 13 of the receiving opening 14.

In the embodiment illustrated in FIG. 1B, the end position is reached when the head 12 of the connection screw 7 rests on a shoulder 71 that runs around on an inner side of the through-bore.

The connection screw 7 is then secured against an undesired release or loosening, and a loss of pre-tension force is prevented. In a preferred embodiment the connection screw 7 further comprises a precision-fit cylinder 15, which is overlapped by an external thread 17. A portion 16 of the receiving opening 14 is formed as a cylindrical precision bore 31, wherein an internal thread runs along the lateral surface of the cylindrical precision bore, so that a perfect fit and/or a threaded connection is formed between the connection screw 7 and the portion 16.

Figure 1C:
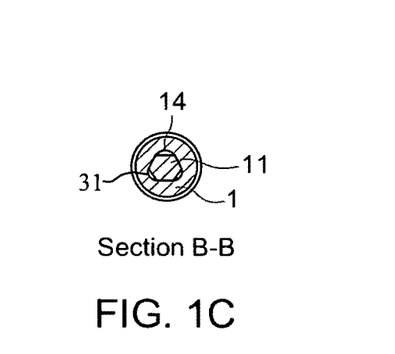
FIG. 1C shows a cross-section through a dental prosthesis system according to FIG. 1A along the axis B-B in a view from above.

FIG. 1C shows a sectional illustration along B-B according to the embodiment from FIG. 1A. What is shown is a cross-section through the receiving opening 14 of the implant 1 in the region of the multi-edged inner profile 13, and a cross-section through the multi-edged outer profile 11. In FIG. 1C the multi-edged outer profile 11 is fully engaged in the multi-edged inner profile 13 in the end position, and three side faces of the multi-edged outer profile lie parallel to the sides of the triangular inner profile. These side faces lie against the sides of the triangular inner profile. As already mentioned with reference to FIG. 1B, the head 12 of the connection screw 7 rests on a shoulder 71 that runs around on an inner side of the through-bore.

The connection screw 7 is secured against rotation and therefore an undesired loosening. In the illustrated embodiment the multi-edged inner profile 13 is formed as a triangular profile and the multi-edged outer profile 11 is formed as a hexagon.

Figure 2A:
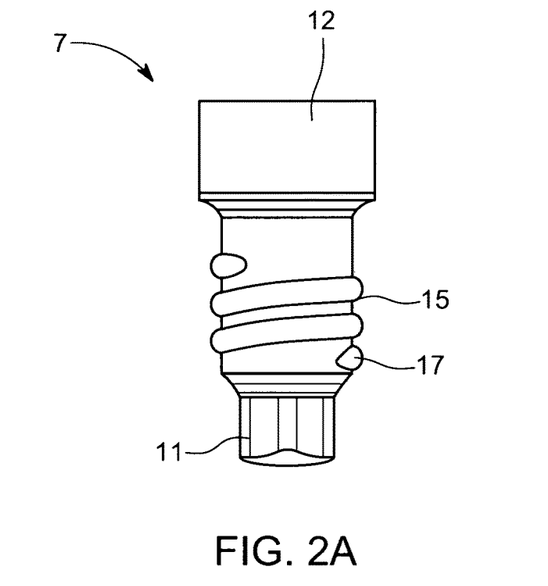
FIG. 2A shows an embodiment of a connection screw in a view from the side.
Figure 2B:
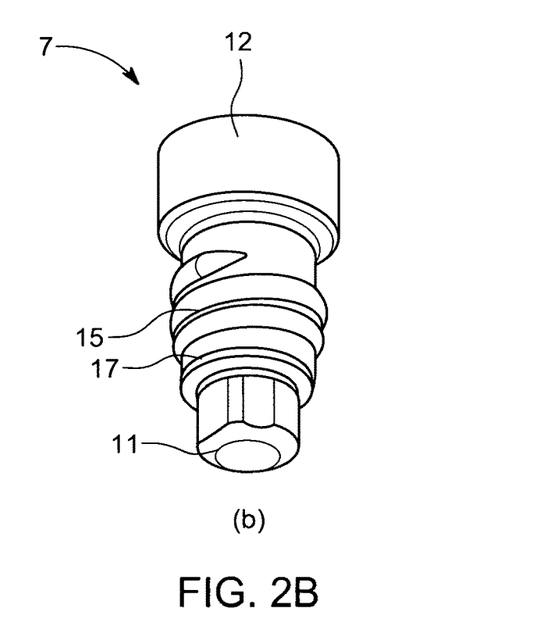
FIG. 2B shows the connection screw from FIG. 2A in a perspective view obliquely from below.

FIGS. 2A and B show two views of the connection screw 7 according to the embodiment from FIGS. 1A-C. The connection screw 7 has the multi-edged outer profile 11, which is formed as a hexagon and is arranged at the proximal end of the connection screw 7. The precision-fit cylinder 15, which is overlapped by the external thread 17, is disposed between the screw head 12 and the multi-edged outer profile 11.

Figure 3A:
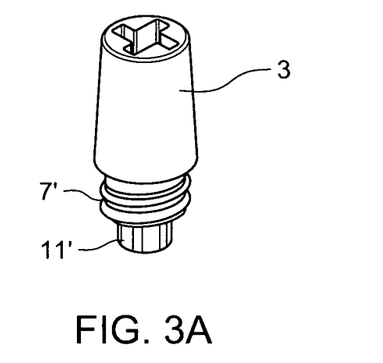
FIG. 3A shows a perspective view of an embodiment, wherein the abutment and connection screw are formed in one piece.
Figure 3B:
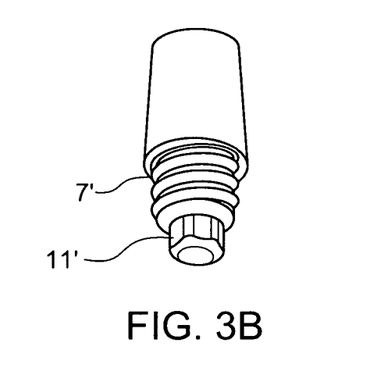
FIG. 3B shows a further perspective view obliquely from above of the embodiment from FIG. 3A obliquely from below.
Figure 3C:
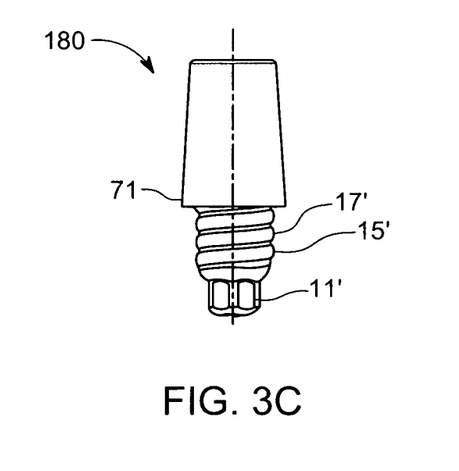
FIG. 3C shows the embodiment from FIG. 3A in a view from the side.

FIGS. 3A-C show three views of a further embodiment according to the invention. The abutment 3 is formed in one piece with the connection screw 7'. The connection screw 7' and abutment 3 form a secondary part 180 for receiving a dental prosthesis, for example a crown or a bridge. In the illustrated embodiment the cylinder, external thread and interlocking means are embodied comparably to those illustrated in FIGS. 2A and B. A multi-edged outer profile 11', in the form of a hexagon, is arranged at the proximal end. Adjacently thereto in the distal direction, there is disposed a precision-fit cylinder 15' with an external thread 17'. In the shown embodiment the secondary part 180 is manufactured from a thermoplastic fibre-reinforced plastic, and the implant is manufactured from a ceramic material (the implant is not shown in FIGS. 3A-C). The multi-edged outer profile 11' engages in a corresponding multi-edged inner profile, arranged in the receiving opening of the implant, when the secondary part 180 is connected to an implant. The multi-edged outer profile 11', which is manufactured in an oversized manner, deforms elastically as it is screwed into the multi-edged inner profile. As a torque is applied to the secondary part 180, the edge regions of the multi-edged outer profile 11' are compressed and relaxed accordingly and engage fully in the multi-edged inner profile in a desired end position. In the present embodiment the screw lock is formed by the conjunction of the multi-edged outer profile 11' on the connection screw 7' and the multi-edged inner profile. The connection of the secondary part 180 to the implant is in this way secured against rotation and therefore against an undesired loosening. A loss of pre-tension force is prevented.

When the abutment according to the embodiment illustrated in FIGS. 3A-C is screwed in, the end position is reached for example when the multi-edged outer profile 11' rests on a surface area of the multi-edged inner profile (not shown in FIGS. 3A-C).

A further possibility for reaching the end position is the resting of the abutment shoulder 71 on the distal end of the implant. If the multi-edged outer profile 11' does not rest on the surface area of the multi-edged inner profile, it is released (not shown in FIGS. 3A-C).

Figure 4A:
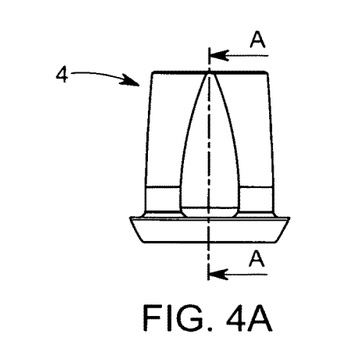
FIG. 4A shows a view of a further embodiment according to the invention of a variant of the abutment with through-bore.
Figure 4B:
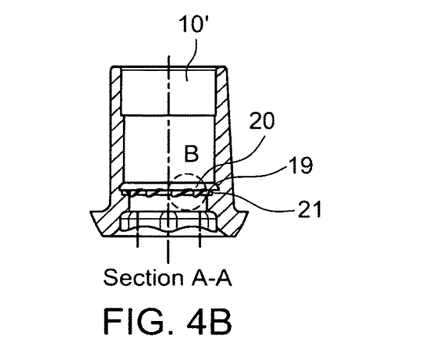
FIG. 4B shows another view of the further embodiment of FIG. 4A.

FIGS. 4A-D show a further embodiment of an abutment 4 which is used in the dental prosthesis system according to the invention. What is illustrated in FIG. 4A is a side view of the abutment 4. FIG. 4B shows a sectional illustration through the abutment 4 along the axis A-A according to FIG. 4A. What is illustrated is a particular embodiment of a through-bore 10'. The through-bore 10', which receives a connection screw for securing the abutment 4 in an implant, has a peripheral structure 19 arranged in the through-bore 10', which structure has protrusions 20. In the embodiment illustrated in FIGS. 4A-D, the structure 19 is formed in one piece with the abutment 4.

Figure 4C:
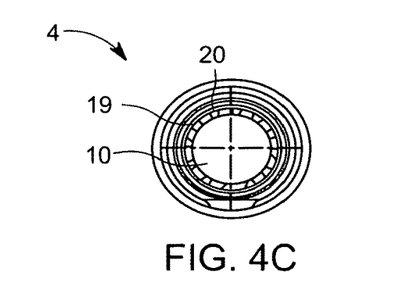
FIG. 4C shows another view of the further embodiment of FIG. 4A.
Figure 4D:
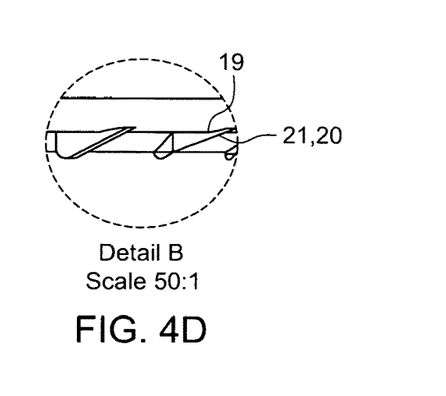
FIG. 4D shows another view of the further embodiment of FIG. 4A.

In the end position the head of the connection screw rests on the structure 19. The first interlocking means, mounted on the head of the connection screw, engage fully in the protrusions 20 in this position (not shown in FIGS. 4A-D). A screw lock is formed and an undesired loosening and a loss of pre-tension force of the connection screw are prevented. In the particular embodiment shown in FIGS. 4B-D, the protrusions 20 are formed as teeth 21. In FIG. 4C the abutment 4 from FIG. 4B is illustrated in a view from above. What is shown is the through-bore 10' with the peripheral structure 19 with the protrusions 20. As in FIG. 4B, the connection screw, which is introduced into the through-bore, is not shown. In FIG. 4D a detail of the protrusions 20 embodied as teeth 21 is illustrated in a side view.

Figure 5A:
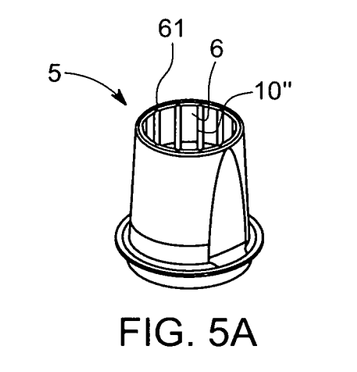
FIG. 5A shows a view of a further embodiment according to the invention of a further variant of the abutment with through-bore.
Figure 5B:
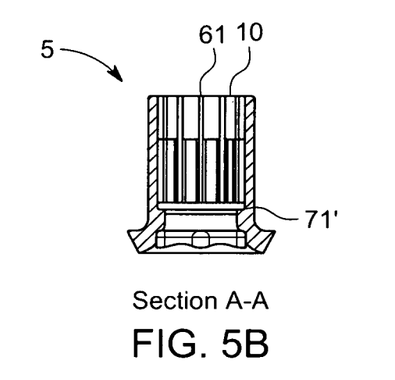
FIG. 5B shows another view of the further embodiment of FIG. 5A.
Figure 5C:
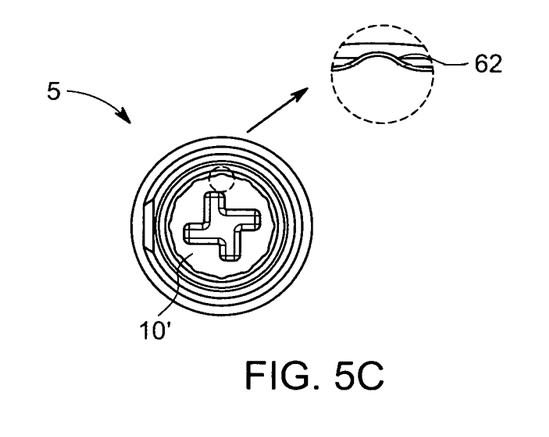
FIG. 5C shows another view of the further embodiment of FIG. 5A.

FIGS. 5A-C show different views of a further embodiment of an abutment 5, as is used in the dental prosthesis system according to the invention. In FIG. 5A the abutment 5 is shown from above in a perspective view. The abutment 5 has a through-bore 10" with second interlocking elements 6, in which first interlocking elements 6' arranged on the head of the connection screw fully engage in an end position (see FIG. 5C). In this position the head of the connection screw rests on a shoulder 71' that runs around on an inner side of the through-bore.

In a preferred embodiment the first and second interlocking elements 6', 6 are formed by ribs and grooves. The grooves run on an inner surface of the through-bore 10" in the longitudinal direction. As a torque is applied and as the desired tightening moment is reached, the first interlocking means 6', formed as ribs 62 on the head of the connection screw 7", engage in the grooves 61 and in this way form a screw lock 90. The connection screw 7" is in this way secured against an undesired loosening, and a loss of pretension force can be prevented. FIG. 5B shows the abutment 5 with through-bore 10" and a plurality of grooves 61 running in the longitudinal direction in a sectional illustration. FIG. 5C shows the abutment 5 with connection screw introduced into the through-bore 10", and a detailed view of an individual rib 62 in an engaged position.

Figure 6A:
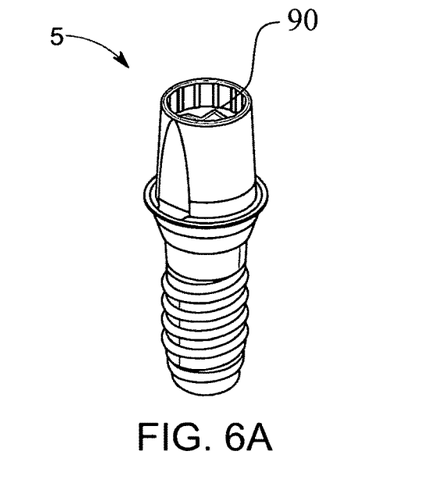
FIG. 6A shows a perspective view of the dental prosthesis system with an abutment from FIG. 5A.
Figure 6B:
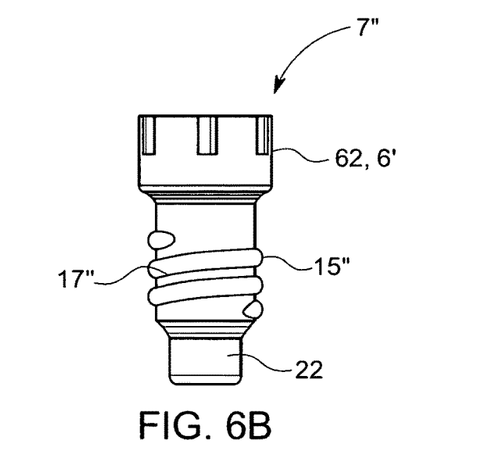
FIG. 6B shows a view of an embodiment of the connection screw, wherein the connection screw is used with the abutment illustrated in FIG. 5A.
Figure 6C:
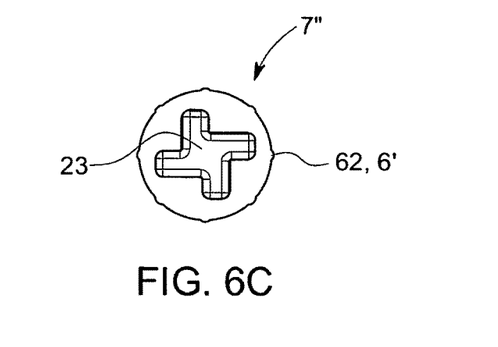
FIG. 6C shows a view of an embodiment of the connection screw, wherein the connection screw is used with the abutment illustrated in FIG. 5A.

FIG. 6A shows a perspective view of the dental prosthesis system according to the invention with the abutment 5 from FIGS. 5A-C. FIG. 6B shows an exemplary embodiment of a connection screw 7", as is used in conjunction with the abutment 5 from FIG. 6A. A plurality of first interlocking means 6', in the form of ribs 62, are arranged on the head of the connection screw 7". In the exemplary embodiment according to FIG. 6B a precision-fit cylinder 15" is shown adjacently to the screw head, as is an external thread 17" overlapping the cylinder. A cylindrical termination element 22 is disposed at the proximal end. FIG. 6C shows the connection screw from FIG. 6B in a view from above, comprising a key grip 23 for a turnkey.

Figure 7A:
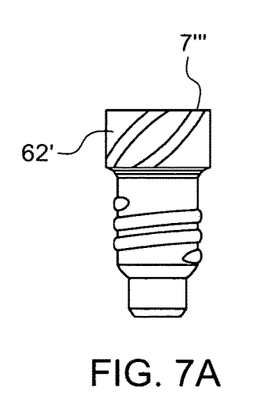
FIG. 7A shows a side view of a further embodiment of a screw for the dental prosthesis system according to the invention.
Figure 7B:
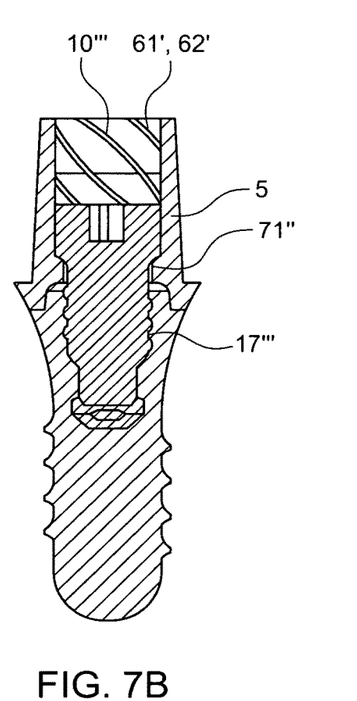
FIG. 7B shows a longitudinal section through an embodiment of the invention, wherein the screw from FIG. 7A is used in the connection of the abutment to the implant.

FIG. 7A shows a further embodiment of a connection screw 7''', and FIG. 7B shows an exemplary embodiment of the dental prosthesis system according to the invention in a sectional illustration, in which the screw 7''' from FIG. 7A is used. In contrast to the embodiment from FIGS. 6A-C, the grooves 61' and ribs 62' on the outer peripheral surface of the screw head and, respectively, the inner peripheral surface of the through bore 10''' are substantially helical. The helix has a steep angle of inclination, which is steeper than the pitch of the external thread 17''' of the connection screw. As a result of this profile, the screw automatically tightens further when the dental prosthesis system is subjected to tensile stress.

In an end position the head of the connection screw lies on a shoulder 71" that runs around on an inner side of the through bore, and the ribs 62' engage fully in the grooves 61' of the inner peripheral surface of the through bore 10'''. Due to the fact that the screw is manufactured from a thermoplastic fibre-reinforced material, the grooves or springs elastically deform as the torque is applied to the screw.

Figure 8:
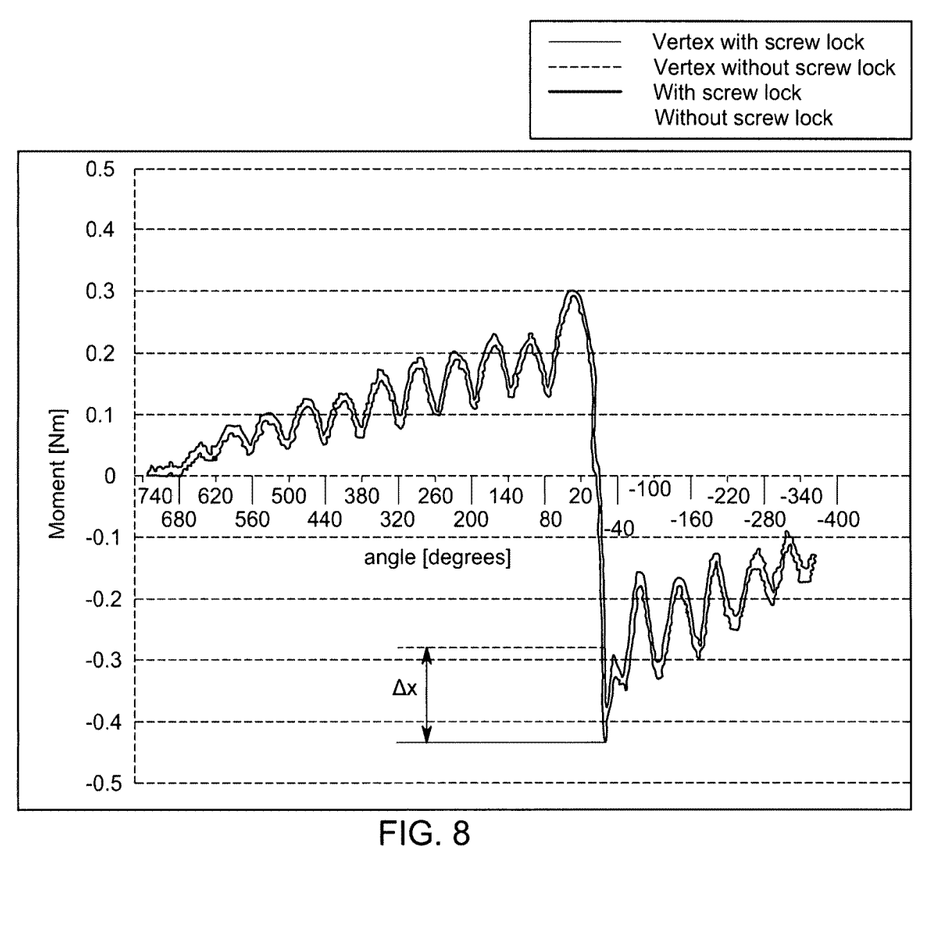
FIG. 8 shows a graph of the course of the tightening moment and of the release moment depending on the rotary angle when tightening and releasing the connection screw in a comparison with and without screw lock according to the embodiment of FIGS. 1A-C, FIG. 9 explains the formula for inner circle radius and outer circle radius, with a schematic showing a triangle symbolizing the triangular inner profile and a hexagon symbolizing the multi-edged external profile.

FIG. 8 shows a graph with the course of the tightening or releasing moment (torque) depending on the rotary angle when the connection screw is tightened or released (for example see the embodiments according to FIGS. 1A-C, FIGS. 2A-B and FIGS. 3A-C). The tightening moment is shown on the positive y-axis. The moment for release is shown on the negative y-axis.

The curve characterized by a solid line represents the course of the torque, wherein the screw lock is formed as a connection screw with a first interlocking means embodied as a hexagonal outer profile, with the second interlocking means being formed as a triangular inner profile in the implant (for example see the embodiments according to FIGS. 1A-C, FIGS. 2A-B and FIGS. 3A-C). Based on these embodiments, the applied torque (y-axis) as the screw is tightened or released assumes an "undulating" course depending on the rotary angle (x-axis) of the connection screw. If the hexagonal outer profile is disposed at a rotary angle to the triangular inner profile at which the edge regions of the hexagonal outer profile are compressed by the side faces of the triangular inner profile, the torque to be applied rises. As the connection screw is rotated further, the rise continues up to a maximum. If a rotary angle is reached at which the outer faces of the multi-edged outer profile are substantially parallel to the faces of the multi-edged inner profile, the torque decreases, and the multi-edged outer profile relaxes and engages fully in the multi-edged inner profile in the end position. The connection screw is rotated until a maximum desired tightening moment, in the present case 30 Ncm (0.3 Nm) is reached. Shortly after this tightening moment has been reached, the multi-edged outer profile relaxes and engages in the triangular inner profile in an end position.

In FIG. 8 the course of the torque as the connection screw is released is shown along the negative y-axis. It is clear from this curve profile that the torque necessary to initially release the connection screw is greater than in the case of a connection screw without a screw lock. In the present case approximately 40 Ncm (0.4 Nm) are necessary in order to unscrew the connection screw from the end position. In the case of the screw without a screw lock, this value is less than 30 Ncm (0.3 Nm). The "delta X" as illustrated in FIG. 8 represents the difference between the vertices of the curved profile with and without screw lock and emphasizes the desired effect to be attained with the dental prosthesis system according to the invention. An undesired release of the connection screw and therefore a loosening of the dental prosthesis system according to the invention can be reliably prevented. As is also the case when the connection screws are tightened, the release moment also runs in an "undulating" manner. The multi-edged outer profile is compressed or relaxed depending on the rotary angle and the cooperation with the multi-edged inner profile.

By way of comparison, the dashed line shows the course of the torque, depending on the rotary angle, of a connection screw without screw lock. Instead of the hexagonal outer profile as a first interlocking means, the connection screw has a cylindrical element. On the basis of the curve profile, it can be seen that there is no elastic deformation of a compression or relaxation of the cylindrical element when this cooperates with the triangular inner profile. The curve rises substantially exponentially until the desired maximum tightening moment is reached, for example 35 Ncm (0.35 Nm). As can be seen from the curved profile in the negative region of the y-axis, the torque necessary to release the connection screw is much smaller than that of a screw with lock. The use of this kind of connection screw is disadvantageous, since the connection screw and therefore the abutment can become loose over the period for which the dental prosthesis system is worn.

Figure 9:
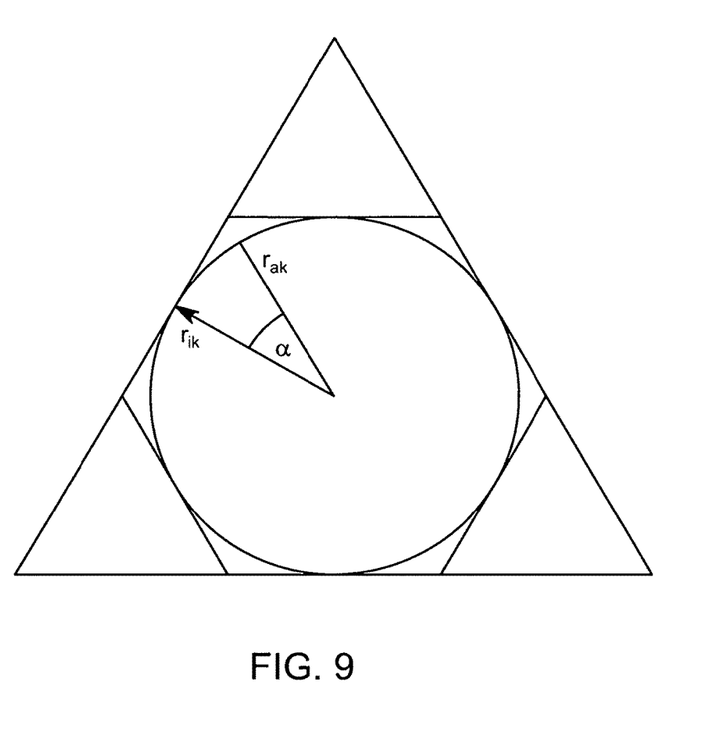

FIG. 9 serves to explain in greater detail the formula for calculating the outer circle radius ($r_a k$) and the inner circle radius ($r_{ik}$) of a schematically illustrated hexagon arranged in a triangle. In the case of the illustrated hexagon, the value for α (alpha) is 30 degrees. FIG. 9 relates to the embodiment explained in FIGS. 1A-C.

The invention claimed is:

1. A dental prosthesis system comprising: a ceramic implant for osseointegration in a jaw bone; a connection screw, wherein the ceramic implant comprises a receiving opening adapted to receive the connection screw; an abutment securable in the receiving opening of the implant (1) by the connection screw (7, 7', 7", 7'''), wherein the connection screw is made of fibre reinforced thermoplastic; and a screw lock, which includes a first interlocking means and a second interlocking means, wherein the first interlocking means is arranged on the connection screw (7, 7', 7", 7''') and the second interlocking means arranged at the receiving opening of the implant, and when tightening or releasing the connection screw (7, 7', 7", 7''') in the implant, the first interlocking means is elastically deformable in conjunction with the second interlocking means; and wherein the first interlocking means is formed as a multi-edged outer profile on the connection screw (7, 7', 7", 7''') and the second interlocking means is formed as a multi-edged inner profile (13) in the receiving opening of the implant, wherein the multi-edged inner profile is preferably formed as a triangular profile.

2. The dental prosthesis system according to claim 1, wherein the first interlocking means in conjunction with the second interlocking means can be compressed or relaxed accordingly as the connection screw is tightened or released.

3. The dental prosthesis system according to claim 2, wherein the first interlocking means is rotatable relative to the second interlocking means, in conjunction with the second interlocking means can be compressed when a first rotary position is reached and can be relaxed when a second rotary position is reached, and the first interlocking means fully engages in the second interlocking means in an end position.

4. The dental prosthesis system according to claim 1, wherein the multi-edged outer profile (11, 11') is arranged on the connection screw (7, 7', 7", 7''') at a screw end opposite a screw head.

5. The dental prosthesis system according to claim 1 wherein the abutment (3) and the connection screw (7') are formed in one piece from fibre-reinforced thermoplastic.

6. The dental prosthesis system according to claim 1 wherein the fibre-reinforced thermoplastic has reinforcement fibres selected from a group consisting of: carbon fibres, aramid fibres, glass fibres, carbon nanotubes, or combinations thereof.

7. The dental prosthesis system according to claim 6, wherein the fibre-reinforced thermoplastic is formed of unidirectional carbon fibres in a PEEK matrix.

8. The dental prosthesis system according to claim 1 wherein a portion of the receiving opening is formed as a cylindrical precision bore (31), wherein the cylindrical precision bore (31) is overlapped by an internal thread in an axial direction based on the rotation axis of the cylindrical precision bore (31), the connection screw (7, 7', 7", 7''') includes a precision-fit cylinder corresponding to the cylindrical precision bore (31) and an external thread corresponding to the internal thread, so that a perfect fit and a threaded connection are formed between connection screw (7, 7', 7", 7''') and receiving opening.

9. A dental prosthesis system comprising: a ceramic implant for osseointegration in a jaw bone; a connection screw, wherein the ceramic implant comprises a receiving opening adapted to receive the connection screw; an abutment, securable in the receiving opening of the implant (1) by the connection screw (7, 7', 7", 7'''), wherein the connection screw is made of fibre reinforced thermoplastic; and a screw lock, which includes a first interlocking means and a second interlocking means, wherein the first interlocking means is arranged on the connection screw (7, 7', 7", 7''') and the second interlocking means arranged at the receiving opening of the implant, and when tightening or releasing the connection screw (7, 7', 7", 7''') in the implant, the first interlocking means is elastically deformable in conjunction with the second interlocking means; wherein the first interlocking means is arranged on a screw head of the connection screw (7, 7', 7", 7''') and the second interlocking means is arranged in a through-bore (10, 10', 10", 10''') of the abutment.

10. The dental prosthesis system according to claim 9, wherein the first interlocking means comprises at least one rib (62) and the second interlocking means comprises at least one groove (61).

11. The dental prosthesis system according to claim 10, wherein the at least one rib (62) is arranged on an outer peripheral surface of the head of the connection screw (7") and the at least one groove (61) is arranged on an inner peripheral surface of the through-bore (10").

12. The dental prosthesis system according to claim 10 wherein the ribs (62) and the grooves (61) run helically.

13. The dental prosthesis system according to claim 10 wherein the at least one rib (62) runs parallel in an axial direction based on a vertical axis of the connection screw and the at least one groove (61) runs parallel in an axial direction based on a vertical axis of the abutment (5).

14. A dental prosthesis system comprising: a ceramic implant for osseointegration in a jaw bone; a connection screw, wherein the ceramic implant comprises a receiving opening adapted to receive the connection screw; an abutment, securable in the receiving opening of the implant (1) by the connection screw (7, 7', 7", 7'''), wherein the connection screw is made of fibre reinforced thermoplastic; and a screw lock, which includes a first interlocking means and a second interlocking means, wherein the first interlocking means is arranged on the connection screw (7, 7', 7", 7''') and the second interlocking means arranged at the receiving opening of the implant, and when tightening or releasing the connection screw (7, 7', 7", 7''') in the implant, the first interlocking means is elastically deformable in conjunction with the second interlocking means; wherein the second interlocking means comprises a structure (19) arranged on an inner peripheral surface of a through-bore (10') of the abutment (4), wherein the structure (19) includes at least one of protrusions (20) and teeth (21).

\* \* \* \* \*